US012806349B2

(12) United States Patent
Nichol et al.

(10) Patent No.: US 12,806,349 B2
(45) Date of Patent: Nov. 24, 2026

(54) DEVICES, SYSTEMS, AND METHODS FOR DELIVERY OF A REPERFUSION-INJURY-MODIFYING DRUG TO A PATIENT

(71) Applicant: University of Washington, Seattle, WA (US)

(72) Inventors: Graham Nichol, Seattle, WA (US); Alberto Aliseda, Seattle, WA (US)

( * ) Notice: Subject to any disclaimer, the term of this patent is extended or adjusted under 35 U.S.C. 154(b) by 771 days.

(21) Appl. No.: 16/978,668

(22) PCT Filed: Mar. 7, 2019

(86) PCT No.: PCT/US2019/021097
§ 371 (c)(1),
(2) Date: Sep. 4, 2020

(87) PCT Pub. No.: WO2019/173561
PCT Pub. Date: Sep. 12, 2019

(65) Prior Publication Data
US 2021/0001062 A1 Jan. 7, 2021

Related U.S. Application Data

(60) Provisional application No. 62/640,461, filed on Mar. 8, 2018.

(51) Int. Cl.
*A61M 15/00* (2006.01)
*A61M 11/00* (2006.01)
*A61M 11/02* (2006.01)

(52) U.S. Cl.
CPC ........ *A61M 15/009* (2013.01); *A61M 11/001* (2014.02); *A61M 11/02* (2013.01);
(Continued)

(58) Field of Classification Search
CPC .. A61M 15/009; A61M 15/00; A61M 11/001; A61M 15/0066; A61M 11/02;
(Continued)

(56) References Cited

U.S. PATENT DOCUMENTS 5,355,872 A * 10/1994 Riggs .................... A61M 16/16 239/338
5,631,234 A 5/1997 Ozawa et al.
(Continued)

FOREIGN PATENT DOCUMENTS

JP 2014-141536 A 8/2014
WO 2007/112403 A2 10/2007
(Continued)

OTHER PUBLICATIONS

Sosunov SA, Ameer X, Niatsetskaya ZV, Utkina-Sosunova I, Ratner VI, Ten VS (2015) Isoflurane Anesthesia Initiated at the Onset of Reperfusion Attenuates Oxidative and Hypoxic-Ischemic Brain Injury. PLoS ONE 10(3): e0120456. https://doi.org/10.1371/journal.pone.0120456 (Year: 2015).*
(Continued)

*Primary Examiner* — Margaret M Luarca
*Assistant Examiner* — Sarah B Lederer
(74) *Attorney, Agent, or Firm* — Nathaniel A. Wickliffe; The Inventor's Friend Patent Law Firm, P.L.L.C.

(57) ABSTRACT

Devices and systems for delivering an aerosolized reperfusion-injury-modifying drug (RIMD) to a patient are described. In an embodiment, the devices include an RIMD; an aerosolizer in fluid communication with the RIMD configured to aerosolize the RIMD to provide an RIMD aerosol; and an exit port configured to direct the RIMD aerosol for receipt by the patient. In an embodiment, the systems include a ventilator configured to generate airflow and coupled to the exit port. Methods for delivering an aerosol
(Continued)

comprising an RIMD to a patient are also described. In an embodiment, the methods include aerosolizing an RIMD to provide an RIMD aerosol comprising RIMD droplets; and introducing the RIMD aerosol into an inhalation airflow of the patient.

27 Claims, 5 Drawing Sheets

(52) U.S. Cl.
CPC ... *A61M 15/0066* (2014.02); *A61M 2202/048* (2013.01); *A61M 2202/0488* (2013.01); *A61M 2205/8206* (2013.01)

(58) Field of Classification Search
CPC . A61M 2202/048; A61K 31/00; A61K 31/08; A61K 31/77; A61K 45/06; A61K 8/046; A61H 31/004; G01N 33/48
See application file for complete search history.

(56) References Cited

U.S. PATENT DOCUMENTS

| | | | | |
|---|---|---|---|---|
| 5,874,064 | A * | 2/1999 | Edwards | A61K 9/0075 424/491 |
| 6,656,452 | B1 | 12/2003 | Zapol et al. | |
| 7,470,898 | B2 | 12/2008 | Merrick et al. | |
| 8,420,380 | B2 | 4/2013 | Fishman et al. | |
| 9,737,486 | B2 | 8/2017 | Bright et al. | |
| 2002/0095044 | A1 | 7/2002 | Jagtap et al. | |
| 2005/0150489 | A1 * | 7/2005 | Dunfield | A61M 15/0083 128/200.14 |
| 2005/0215333 | A1 | 9/2005 | Gottlieb et al. | |
| 2008/0072895 | A1 * | 3/2008 | Ganan-Calvo | A61M 16/14 128/200.22 |
| 2012/0016252 | A1 * | 1/2012 | Melker | A61B 5/4821 600/532 |
| 2014/0048061 | A1 * | 2/2014 | Yannopoulos | A61M 16/18 128/200.14 |
| 2014/0053831 | A1 * | 2/2014 | Leamon | A61M 11/042 128/200.14 |
| 2016/0030692 | A1 * | 2/2016 | Burk | A61M 16/0093 128/200.14 |
| 2016/0263051 | A1 * | 9/2016 | Pretto | A61K 47/34 |
| 2016/0346323 | A1 | 12/2016 | Roth et al. | |

FOREIGN PATENT DOCUMENTS

| | | | |
|---|---|---|---|
| WO | 2012/019076 | A1 | 2/2012 |
| WO | 2013/171332 | A2 | 11/2013 |
| WO | 2017027810 | A2 | 2/2017 |

OTHER PUBLICATIONS

International Search Report and Written Opinion, dated May 13, 2019, for International Patent Application No. PCT/US2019/021097. (8 pages).
Sosunov, S.A. et al., "Isoflurane Anesthesia Initiated at the Onset of Reperfusion Attenuates Oxidative Isoflurane Anesthesia Initiated at the Onset of Reperfusion Attenuates Oxidative and Hypoxic-Ischemic Brain Injury," PLoS One, 10(3):1-15, 2015.
Cavalcante, F.P. et al., "Mechanisms of the beneficial effect of sevoflurane in liver ischemia/reperfusion injury," Acta Cirugica Brasileira, 30(11):749-755, 2015.
Ikeda, G. et al., "Nanoparticle-Mediated Targeting of Cyclosporine A Enhances Cardioprotection Against Ischemia-Reperfusion Injury Through Inhibition of Mitochondrial Permeability Transition Pore Opening," Scientific Reports, 6:20467, pp. 1-13, 2016.
Chang, S-T. et al., "Platelet Glycoprotein IIb/IIIa Inhibitor Tirofiban Ameliorates Cardiac Reperfusion Injury," International Heart Journal, 56(3):335-340, 2015.
Magruder, J.T. et al., "Imatinib Is Protective Against Ischemia-Reperfusion Injury in an Ex Vivo Rabbit Model of Lung Injury Author links open overlay panel," Annals of Thoracic Surgery, 105(3):950-956, 2018.
Jacobs, I. et al., "Cardiac arrest and cardiopulmonary resuscitation outcome reports: update and simplification of the Utstein templates for resuscitation registries. A statement for healthcare professionals from a task force of the international liaison committee on resuscitation," Resuscitation, 63(3):233-249, 2004.
Benjamin, E.J. et al., "Heart Disease and Stroke Statistics—2017 Update: A Report From the American Heart Association," Circulation, 135(10):e146-e603, 2017.
Nichol, G. et al., "Regional variation in out-of-hospital cardiac arrest incidence and outcome," JAMA, 300(12):1423-1431, 2008.
Stiell, I.G. et al., "Early versus later rhythm analysis in patients with out-of-hospital cardiac arrest," N. Engl. J. Med., 365(9):787-797, 2011.
Nichol, G. et al., "Trial of Continuous or Interrupted Chest Compressions during CPR," N. Engl. J. Med., 373(23):2203-2214, 2015.
Yellon, D.M. and Hausenloy, D.J., "Myocardial reperfusion injury," N. Engl. J. Med., 357(11):1121-1135, 2007.
Madathil, R.J. et al., "Ischemia reperfusion injury as a modifiable therapeutic target for cardioprotection or neuroprotection in patients undergoing cardiopulmonary resuscitation," Resuscitation, 105:85-91, 2016.
Adrie, C. et al., "Successful cardiopulmonary resuscitation after cardiac arrest as a "sepsis-like" syndrome," Circulation, 106(5):562-568, 2002.
Bisschops, L. et al., "Seventy-two hours of mild hypothermia after cardiac arrest is associated with a lowered inflammatory response during rewarming in a prospective observational study," Crit. Care, 18(5):546; 2014.
Gando, S. et al., "Massive fibrin formation with consecutive impairment of fibrinolysis in patients with out-of-hospital cardiac arrest," Thromb. Haemost., 77(2):278-282, 1997.
Miura, T. and Tanno, M., "The mPTP and its regulatory proteins: final common targets of signalling pathways for protection against necrosis," Cardiovasc. Res., 94(2):181-189, 2012.
Peart, J.N. and Headrick, J.P., "Clinical cardioprotection and the value of conditioning responses," Am. J. Physiol. Heart and Circ. Physiol., 296(6):H1705-H1720, 2009.
Gonzalez, M.M. et al., "Left ventricular systolic function and outcome after in-hospital cardiac arrest," Circulation, 117(14):1864-1872, 2008.
Kern, K.B. et al., "Myocardial microcirculatory dysfunction after prolonged ventricular fibrillation and resuscitation," Crit. Care Med., 36(11 Suppl):S418-421, 2008.
Idris, A.H. et al., "Oxidant injury occurs rapidly after cardiac arrest, cardiopulmonary resuscitation, and reperfusion," Crit. Care Med., 33(9):2043-2048, 2005.
Kern, K.B. et al., "Myocardial cytokine IL-8 and nitric oxide synthase activity during and after resuscitation: preliminary observations in regards to post-resuscitation myocardial dysfunction," Resuscitation, 77(3):401-409, 2008.
Vaahersalo, J. et al., "Admission interleukin-6 is associated with post resuscitation organ dysfunction and predicts long-term neurological outcome after out-of-hospital ventricular fibrillation," Resuscitation, 85(11):1573-1579, 2014.
Green, A.R. and Shuaib, A., "Therapeutic strategies for the treatment of stroke," Drug Discovery Today, 11(15/16):681-693, 2006.
Laurent, I. et al., "Reversible myocardial dysfunction in survivors of out-of-hospital cardiac arrest," J. Am. Coll. Cardiol., 40(12):2110-2116, 2002.
Bickler, P.E. and Fahlman, C.S., "Enhanced hypoxic preconditioning by isoflurane: signaling gene expression and requirement of intracellular Ca2+ and inositol triphosphate receptors," Brain Res., 1340:86-95, 2010.
Yu, Q. et al., "Neuroprotections and mechanisms of inhalational anesthetics against brain ischemia," Front Biosci. (Elite Ed)., 2:1275-1298, 2010.
Liu, J. et al., "Isoflurane reduces oxygen-glucose deprivation-induced oxidative, inflammatory, and apoptotic responses in H9c2 cardiomyocytes," Am. J. Transl. Res., 8(6):2597-2608, 2016.

(56) References Cited

OTHER PUBLICATIONS

Li, H. and Lang, X.E., "Protein kinase C signaling pathway involvement in cardioprotection during isoflurane pretreatment," Mol. Med. Rep., 11(4):2683-2688, 2015.
Lang, X.E. et al., "Mechanisms of cardioprotection by isoflurane against I/R injury," Front Biosci. (Landmark Ed)., 18:387-393, 2013.
Xu, X. et al., "miR-21 in ischemia/reperfusion injury: a double-edged sword?" Physiol. Genomics, 46(21):789-797, 2014.
Hoerauf, K. et al., "Genetic damage in operating room personnel exposed to isoflurane and nitrous oxide," Occup. Environ. Med., 56(7):433-437, 1999.

* cited by examiner

DEVICES, SYSTEMS, AND METHODS FOR DELIVERY OF A REPERFUSION-INJURY-MODIFYING DRUG TO A PATIENT

CROSS-REFERENCE TO RELATED APPLICATION

This application claims the benefit of U.S. Provisional Application No. 62/640,461, filed Mar. 8, 2018, the content of which is hereby incorporated by reference in its entirety.

BACKGROUND

Out-of-hospital cardiac arrest (OHCA) is an unexpected pulseless condition attributable to cessation of cardiac mechanical activity in the field. About 356,000 individuals experience OHCA annually in the United States. Of these, about 75,800 have a first recorded rhythm that is ventricular fibrillation (VF), which hereafter includes pulseless ventricular tachycardia or shockable by an automated external defibrillator (AED) Underlying mechanisms for non-traumatic cardiac arrest include a) conductive abnormalities of the myocardium leading to arrhythmias, b) chronically weakened myocardium leading to end-stage pump failure, and c) acute occlusion of a coronary artery leading to myocardial infarction. Of these mechanisms, resuscitation is generally most successful for isolated conductive abnormalities or for acute coronary thrombosis that is treated rapidly. Acute occlusion is most common among those patients with VF. Thus, OHCA is commonly categorized by the first recorded rhythm: VF, pulseless electrical activity, or asystole. Treatment given and probability of survival under current standards of care depend heavily on this categorization. Treatment begins in the field, and then transitions to the emergency department of a receiving hospital before continuation in multiple locations throughout the hospital.

Existing treatments for OHCA combine cardiopulmonary resuscitation (CPR) and early defibrillation by bystanders or first responders, with advanced life support by emergency medical services (EMS) providers that includes CPR, defibrillation and intravenous drugs, and post-resuscitation care in hospital. About 12 to 15% of EMS-treated OHCA survive to discharge; about 33 to 50% of those with a spontaneous blood pressure upon emergency department (ED) arrival survive.

Quick restoration of blood flow reduces the chance of death after OHCA occurs. This restoration of flow (called reperfusion) causes release of circulating inflammatory molecules that lead to cellular injury. This reperfusion injury (RI) includes rapid release of reactive oxygen species (ROS), cytokines, adhesion molecules and leukocytes, upregulation of deoxyribonucleic acid (DNA) for gene expression, endothelial dysfunction, and opening of mitochondrial permeability transition pores (MPTP). The latter plays a key role in myocardial necrosis.

After restoration of spontaneous circulation (ROSC), there is a period of myocardial depression that is particularly harmful to the heart. This is associated with the elevation of ROS levels which peak within 30 minutes after reperfusion and have normalized within 90 minutes. Likewise, elevation of inflammatory cytokines that begins upon ROSC generally persists for at least six hours post-resuscitation. This period of myocardial depression may be temporary (i.e., myocardial stunning) or may progress to myocyte death, and correlates with the period of significant post-arrest mortality. Non-survivors have serum cytokine levels 20-fold greater than survivors. The extent of RI correlates with how long a patient lacked blood flow, and how likely they are to survive.

In the brain, RI is associated with activation of N-methyl-D-aspartate receptors; opening of MPTPs; impaired oxygen and glucose metabolism; release of free radicals, ROS, and cytokines; and seizures. In the heart, RI is associated with activation of glutamate receptors; opening of MPTPs; impaired oxygen and glucose metabolism; release of free radicals and ROS; microvascular obstruction; myocardial dysfunction; and arrhythmia. In both organs, these adverse cellular changes are associated with programmed cell death, which is commonly called apoptosis. The myocardial depression observed after ROSC usually resolves within 24 hours.

Effective treatments should begin as soon as feasible and continued as patients are transported to the ED or to multiple locations through-out the hospital so as to have preferred impact on RI. There are presently limited options for treatment of RI, particularly in settings outside of a hospital.

SUMMARY

Toward that end, the present disclosure provides devices, systems, and methods for delivering reperfusion-injury-modifying drugs (RIMDs) to a patient. As discussed further herein, such RIMDs may be delivered in the form of an RIMD aerosol including a plurality of RIMD droplets and may be used outside of a hospital or other medical facility, such as during emergent treatment of reperfusion injury.

Accordingly, in an aspect, the present disclosure provides a device for delivering an aerosolized RIMD to a patient. In an embodiment, the device generally includes an RIMD; an aerosolizer in fluid communication with the RIMD configured to aerosolize the RIMD to provide an RIMD aerosol; and an exit port configured to direct the RIMD aerosol for receipt by the patient.

In another aspect, the present disclosure provides a system for delivering an aerosolized RIMD to a patient. In an embodiment the system generally includes an RIMD; an aerosolizer in fluid communication with the RIMD configured to aerosolize the RIMD to provide an RIMD aerosol; and a ventilator configured to generate airflow and coupled to an exit port configured to transport the RIMD aerosol to the patient.

In an embodiment, the system includes a vaporizer suitable to deliver an RIMD to a patient beginning in the out-of-hospital setting.

In an embodiment, the system includes a metered-dose inhaler configured to deliver a fixed dose of a RIMD to a patient beginning in the out-of-hospital setting.

In an embodiment, the system includes a filter configured to sequester RIMD not delivered to, or in exhaled breath from, a patient.

In yet another aspect, the present disclosure provides a method of delivering an aerosol comprising an RIMD to a patient. In an embodiment, the method generally includes aerosolizing an RIMD to provide an RIMD aerosol comprising RIMD droplets; and introducing the RIMD aerosol into an inhalation airflow of the patient.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The present disclosure provides examples of devices, systems, and methods for delivery of reperfusion-injury-modifying drugs (RIMDs) to a patient. As set forth in greater detail below, such devices and systems are configured to provide and such methods provide an RIMD aerosol, such as by aerosolizing a liquid RIMD, for introduction into an inhalation airway of the patient.

Many conventional drug delivery systems for patient inhalation deliver drug vapors generated at a liquid-gas interface. Such conventional drug delivery systems are typically large and very heavy and, as such, are limited to use in hospital settings. In this regard, they are generally unsuitable for use outside of hospitals, such as in an ambulance or other out-of-hospital settings for emergency use.

As discussed further herein, effective treatment of reperfusion injury should begin soon after blood flow is reestablished. Toward this end, the present disclosure provides devices, systems, and methods suitable to provide an RIMD aerosol to a patient, such as a patient suffering from or suspected of suffering from reperfusion injury, for example after myocardial infarction, cardiac arrest, or stroke. As discussed further herein, such RIMD aerosols are suitable to facilitate rapid absorption via the lung into the blood. Further, the devices described herein, which include an aerosolizer, are suitable for use outside of a hospital setting. In many instances, treatment of reperfusion injury yields better results when administered relatively soon after diagnosis. In this regard, the portable devices of the present disclosure are suitable for such rapid patient treatment where diagnosis of reperfusion injury may occur.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. Further, it will be appreciated that embodiments of the present disclosure may employ any combination of features described herein.

Devices

Figure 1:
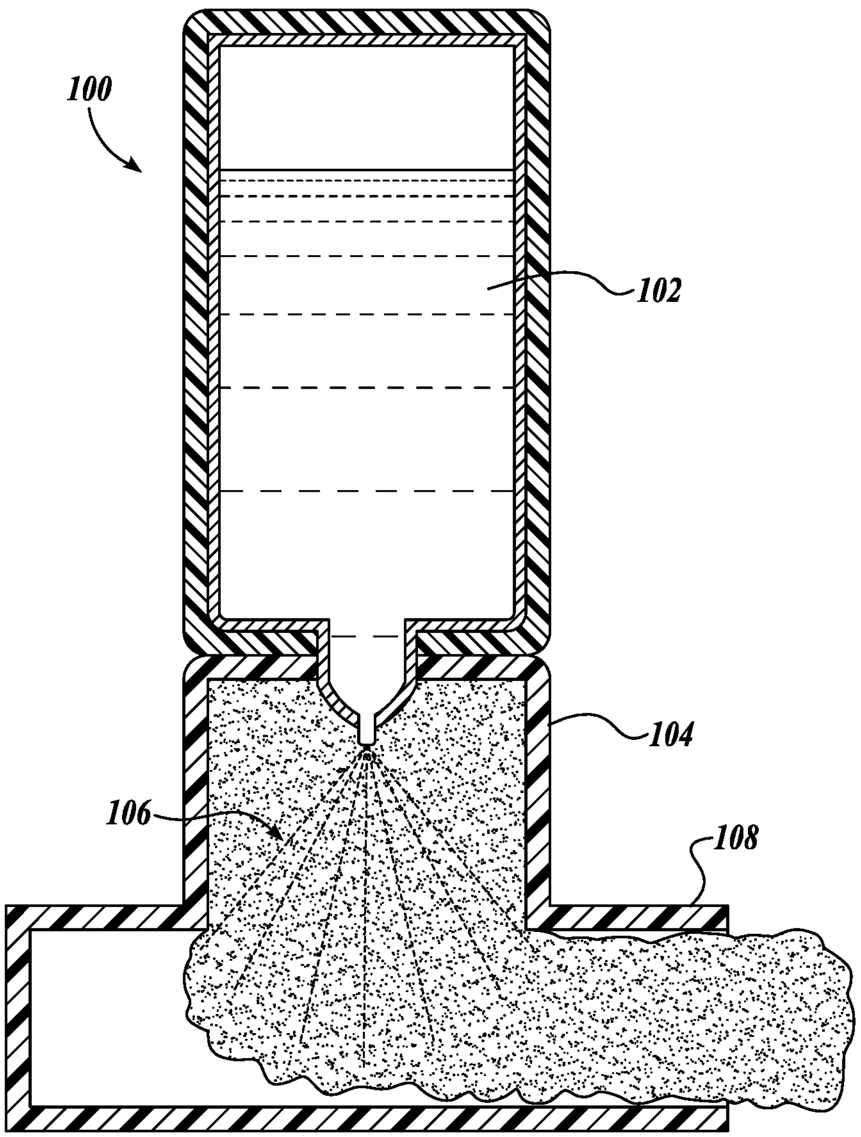
FIG. 1 is a cross-section view of a device, in accordance with an embodiment of the disclosure.

In an aspect, the present disclosure provides a device for delivering an aerosolized RIMD to a patient. In that regard, attention is directed to FIG. 1 in which a device 100, in accordance with an embodiment of the disclosure, is illustrated. In the illustrated embodiment, the device 100 includes an RIMD 102 shown as a liquid disposed in a container; an aerosolizer 104 in fluid communication with the RIMD 102 configured to aerosolize the RIMD 102 to provide an RIMD aerosol 106; and an exit port 108 configured to direct the RIMD aerosol 106 for receipt by the patient via a mask, supraglottic airway, endotracheal tube or other airway. As shown, the RIMD 102 is disposed in fluid communication with the aerosolizer 104 such that the aerosolizer 104, in operation, can generate the RIMD aerosol 106 including RIMD 102 liquid droplets. In the illustrated embodiment, the RIMD aerosol 106 is directed by the exit port 108 for receipt by a patient in fluid communication with the exit port 108.

As used herein, an "RIMD" refers to a composition or mixture of compositions that, when administered to a patient, is/are suitable to treat reperfusion injury, such as to ameliorate, palliate, lessen, and/or delay one or more of its symptoms, such as those symptoms described herein above. In an embodiment, the RIMD 102 is a fluorinated anesthetic. As used herein, a "fluorinated anesthetic" refers to a compound having anesthetic properties when administered to a patient, the compound containing one or more fluorine atoms. In an embodiment, the RIMD 102 is selected from the group consisting of isoflurane, sevoflurane, desflurane, methoxyflurane, and combinations thereof. In an embodiment, the RIMD 102 is mixed with an additive selected from the group consisting of pharmacologically acceptable carriers, vehicles, solvents, diluents, coloring agents, preservatives, neutralizers and stabilizers, and combinations thereof. In an embodiment, the RIMD 102 includes one or more surfactants suitable to reduce RIMD droplet surface tension and to make smaller RIMD droplets. In an embodiment, the RIMD 102 includes one or more solvents suitable to reduce a solution viscosity and to make smaller RIMD droplets. In an embodiment, the RIMD 102 includes one or more chemical additives suitable to speed up evaporation of RIMD droplets.

In an embodiment, the RIMD 102 is a liquid at room temperature and atmospheric pressure and not readily miscible with water. As used herein, "room temperature" refers to a temperature of about 23° C. As used herein, "atmospheric pressure" refers to a pressure of about 1 atm. As discussed further herein, the device 100 is configured to generate an RIMD aerosol 106. An RIMD aerosol 106, such as an RIMD aerosol 106 formed from an RIMD 102 that is a liquid at room temperature and atmospheric pressure and immiscible with water, is suitable to be transported deep into lungs of the patient when introduced into an inhalation airway. Liquid RIMD 102 droplets made therefrom generally vaporize within the lungs. In this regard, there is no need to pre-vaporize the RIMD 102, such as is done with conventional drug delivery devices for, for example, inhaled anesthetics. Moreover, an RIMD aerosol 106 dosage is consistent with delivery of a prescribed value and constant in time. This is in contrast to pre-vaporization methods in which different degrees of mixing with ambient air can lead to large variations in concentration in the gas mixtures.

As above, the device 100 is configured to aerosolize an RIMD 102 to provide an RIMD aerosol 106. As used herein, an "aerosolizing" refers to the process of generating an aerosol and includes atomizing, misting, and the like to transform a continuous liquid into a plurality of liquid droplets in a gas. In that regard, the RIMD aerosol 106 includes a plurality of RIMD 102 liquid droplets dispersed in a gas, such as air. Such an RIMD aerosol 106 is in contrast to an RIMD vapor in which an RIMD is in a gas phase and does not include RIMD 102 liquid droplets. While the RIMD 102 droplets of an RIMD aerosol 106 eventually evaporate, the devices and systems of the present disclosure are configured to deliver an RIMD aerosol 106 to a patient rather than an RIMD 102 vapor.

In an embodiment, the device 100 includes a metered-dose inhaler configured to deliver a fixed dose of the RIMD aerosol 106. Such a device 100 can be used to deliver fixed dose of RIMD aerosol 106 with a simple user input. In that regard, the device 100 is suitable for use in out-of-hospital settings and for administration by, for example, emergency medical technicians, as well as doctors, nurses, and the like in hospitals.

As above, in an embodiment, the device 100 includes an aerosolizer 104 configured to provide such an RIMD aerosol 106 from an RIMD 102 in fluidic contact with the aerosolizer 104. In that regard, attention is directed to FIG. 4 in which an aerosolizer 404, in accordance with an embodiment of the disclosure is illustrated. In the illustrated embodiment, the aerosolizer 404 includes a needle 424 defining a lumen 426 in fluid communication with an RIMD 402 and a sheath gas source 430 coaxially disposed about a major axis 432 of the needle 424. Such an aerosolizer 404 is generally smaller and/or lighter than a conventional device used to vaporize a drug for inhalation by a patient. Accordingly, in an embodiment, the aerosolizer 404 is suitable for use, such as in generating and delivering RIMD aerosols in out-of-hospital settings. In that regard, in an embodiment, the aerosolizer 404 is an example of the aerosolizer 104 of device 100.

While the sheath gas is illustrated as moving coaxially about major axis 432 of the needle 424, it will be understood that other liquid-gas angles are possible to generate the RIMD aerosol 406. In an embodiment, the aerosolizer 404 includes a gas source positioned to move gas across a distal end of the needle 424 at an angle in a range of about 0° to about 180° and at a gas speed suitable to generate the RIMD aerosol 406. Further, while gas-based aerosolizers 404 are described, it will be understood that the devices and systems of the present disclosure include aerosolizers configured to generate an RIMD aerosol based upon, for example, acoustics and/or electrostatics forcing the liquid RIMD to form RIMD droplets, such as without gas flow.

In operation, the sheath gas source 430 directs sheath gas about a distal end of the needle 424 as the liquid RIMD 402 is ejected from the distal end of the needle 424. In this regard, liquid droplets 428 of the RIMD 402 are generated as the liquid RIMD 402 is exposed to shear forces from the sheath gas. Such an aerosolizer 404 is configured to controllably and reproducibly generate RIMD liquid droplets 428 and aerosols 406 including such RIMD liquid droplets 428.

As discussed further herein with respect the methods of the present disclosure, RIMD aerosol 406 having generally smaller droplets are suitable to provide vaporized RIMD 402 to lungs of a patient. In this regard, the RIMD 402 is absorbed quickly into the patient bloodstream via the lungs. Further, such relatively small RIMD liquid droplets 428 are less likely than droplets having a larger size to impinge onto an epithelial surface of the patient's airway, which is generally toxic to the patient.

Accordingly, in an embodiment, the aerosolizer 404 is configured to provide an RIMD aerosol 406 including droplets 428 of the RIMD 402 having an average diameter of less than about 25 μm. In an embodiment, the aerosolizer 404 is configured to provide an RIMD aerosol 406 including droplets 428 of the RIMD 402 having an average diameter of less than about 15 μm. In an embodiment, the aerosolizer 404 is configured to provide the RIMD aerosol 406 including droplets 408 of the RIMD 402 having an average diameter in a range of about 10 μm to about 20 μm.

Such relatively small liquid RIMD droplets 428 may be generated by, for example, manipulating an inner diameter of the lumen 426 of the needle 424 and/or a gas speed of the sheath gas. In an embodiment, an inner diameter of the lumen 426 of the needle 424 is less than 1 mm. In an embodiment, the inner diameter of the lumen 426 of the needle 424 is in a range of about 0.1 mm to about 1 mm. In an embodiment, a gas speed of the sheath gas is in a range of about 20 m/s to about 100 m/s. In an embodiment, the gas speed of the sheath gas is about 40 m/s.

Referring again to FIG. 1, the device 100 includes an exit port 108 configured to direct an RIMD aerosol 406 for receipt by the patient. In this regard, the exit port 108 is in fluid communication with the aerosolizer 104 to receive and direct RIMD aerosol 106 generated therefrom. In an embodiment, the exit port 108 is configured to couple with a supraglottic airway or an endotracheal tube. See, for example, FIG. 2. Such devices coupleable to the exit port 108 are suitable to deliver the RIMD aerosol 106 from the exit port 108 for introduction into a patient inhalation airway.

In an embodiment, the exit port 108 is couplable to a ventilator. See FIG. 2. In this regard, RIMD aerosol 106 generated by the device 100 is carried by airflow generated by the ventilator and into an inhalation airflow of the patient. Such a ventilator may be used to augment or replace a patient's own inhalation, such as when a patient is incapacitated. In this regard, the device 100 is suitable to deliver the RIMD aerosol 106 to an incapacitated patient experiencing or at risk of experiencing reperfusion injury.

Systems

In another aspect, the present disclosure provides a system for delivering an aerosolized RIMD to a patient. In that regard, attention is directed to FIG. 2 in which a system 200, in accordance with an embodiment of the disclosure, is illustrated. In the illustrated embodiment, the system 200 includes an RIMD 202; an aerosolizer 204 in fluid communication with the RIMD 202 configured to aerosolize the RIMD 202 to provide an RIMD aerosol 206; and a ventilator 212 configured to generate airflow and coupled to an exit port 208 configured to transport the RIMD aerosol 206 to the patient. As shown, the RIMD 202 is in fluid communication with the aerosolizer 204, which generates the RIMD aerosol 206. In an embodiment, aerosolizer 204 is the aerosolizer 404 of FIG. 4.

The exit port 208, shown here coupled to an endotracheal tube 214, directs the RIMD 202 for receipt by a patient (not shown), such as by directing the RIMD aerosol 206 into a patient inhalation airway. While an endotracheal tube 214 is shown, it will be understood that other patient airway interface devices are possible. In this regard, the exit port 208 may be configured to couple with, for example, a supraglottic airway (not shown).

In an embodiment, the exit port 208 is coupled with a portable ventilatory assist device, such as a ventilator 212, configured to generate airflow to transport the RIMD aerosol 206 to the patient. In the illustrated embodiment, the system 200 includes a ventilator 212 coupled to the exit port 208 on a side of the exit port 208 opposite the endotracheal tube 214. In this regard, airflow generated by the ventilator 212 is configured to transport the RIMD aerosol 206 through the exit port 208 and into the endotracheal tube 214 for receipt by the patient.

In an embodiment, the ventilator 212 is a portable ventilator 212 configured to be used outside of a hospital setting. In this regard, the ventilator 212 may be, for example, of a size, shape, and weight suitable to be carried and operated outside of a hospital setting, such as in during operation of the system 200 to treat a patient experiencing or suspected of experiencing reperfusion injury. In an embodiment, such a portable ventilator 212 has a weight low enough to be carried, for example, by an emergency medical technician to and from an ambulance. In an embodiment, the portable ventilator 212 is of a size configured to fit inside of an ambulance. In an embodiment, the portable ventilator 212 is powered by compressed gas and/or an electric power source (not shown).

In an embodiment, the ventilator 212, RIMD 202, and aerosolizer 204 are integrated into a single unit, such as within a single housing. In an embodiment, the system 200 includes a ventilator 212, such as a conventional ventilator 212, coupled to an aerosolizer 204, such as through an exit port 208.

The illustrated system 200 is shown to further include a gas monitor 216 configured to contact breath exhaled by the patient. In an embodiment, the gas monitor 216 is configured to generate a signal based on an amount of RIMD 202 in the exhaled breath. In this regard, the gas monitor 216 is configured to sample breath exhaled by the patient for RIMD 202 levels and/or concentrations. Such exhaled RIMD 202 can be an indication of an amount of RIMD 202 in a patient and may provide information regarding whether to increase or decrease an amount of RIMD aerosol 206 provided to the patient. As shown, the gas monitor 216 is operatively coupled to a controller 220, such as to exchange signals between the gas monitor 216 and the controller 220. In an embodiment, the controller 220 includes logic that, when executed by the controller 220, causes the system 200 to perform operations including changing an amount of RIMD aerosol 206 generated by the aerosolizer 204 based on the signal generated by the gas monitor 216.

Figure 2:
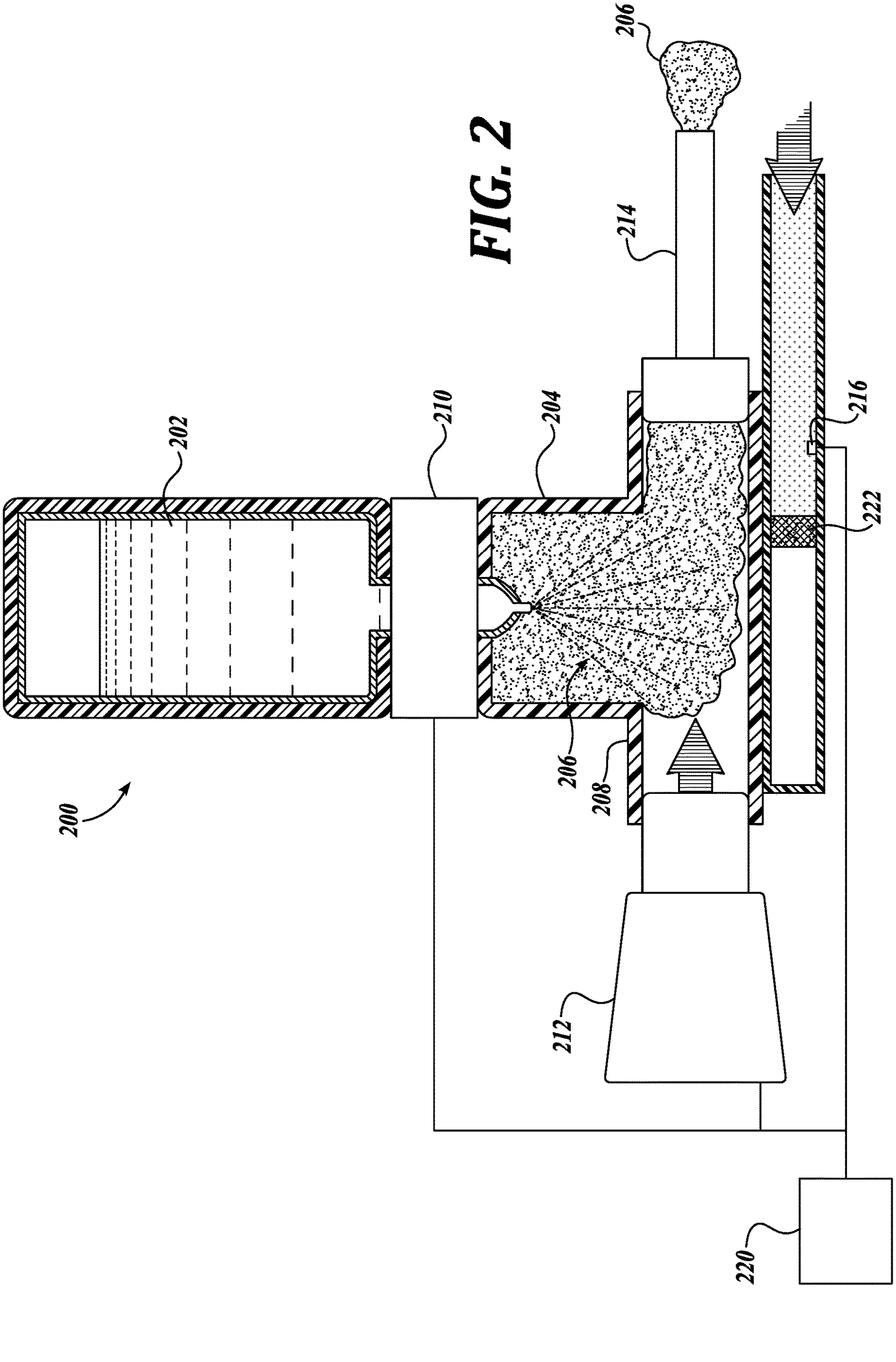
FIG. 2 is cross-section view of a system, in accordance with an embodiment of the disclosure.

The controller 220 is shown coupled to various components of the system 200 to choreograph their operation. Controller 220 may include software/firmware logic executing on a microcontroller, hardware logic (e.g., application specific integrated circuit, field programmable gate array, etc.), or a combination of software and hardware logic. Although FIG. 2 illustrates controller 220 as a distinct functional element, the logical functions performed by controller 220 may be decentralized across a number hardware elements. Controller 220 may further include input/output (I/O ports), communication systems, or otherwise.

The system 200 is further shown to include a pump 210 configured to deliver the RIMD 202 to the aerosolizer 204. In the illustrated embodiment, the pump 210 is disposed between the RIMD 202 and the aerosolizer 204, such as to deliver the RIMD 202 to the aerosolizer 204 is a controlled manner. The pump 210 is also shown operatively coupled to the controller 220. In an embodiment, changing the amount of RIMD aerosol 206 generated by the aerosolizer 204 includes changing a rate at which the pump 210 delivers the RIMD 202 to the aerosolizer 204, such as based upon instructions from the controller 220 delivered to the pump 210. In an embodiment, such instructions are based upon the signal from the gas monitor 216.

In an embodiment, the pump 210 is selected from the group consisting of a peristaltic pump, a rotary vane pump, a piston pump, a screw pump, and a plunger pump.

As above, the ventilator 212 is also shown operatively coupled to the controller 220. In an embodiment, changing the amount of RIMD aerosol 206 includes changing an amount of airflow generated by the ventilator 212, such as based upon instructions from the controller 220 delivered to the ventilator 212. In an embodiment, such instructions are based on the signal from the gas monitor 216.

In an embodiment, the system 200 includes structures for sequestering RIMD 202 in an exhalation airflow of the patient. RIMD 202, such as fluorinated anesthetics, may be toxic to or affect health care providers and/or patient, such as if the health care providers and/or the patient are exposed to the exhaled RIMD 202 for an extended period of time. As shown, the system 200 includes a filter 222 for sequestering RIMD 202 in the exhalation airflow, such as to eliminate or mitigate exhaled RIMD 202 in an airspace of health care providers and/or the patient. In an embodiment, the filter 222 includes activated charcoal or other compounds configured to sequester RIMD 202 vapor and/or RIMD 202 liquid droplets.

Methods

Figure 3:
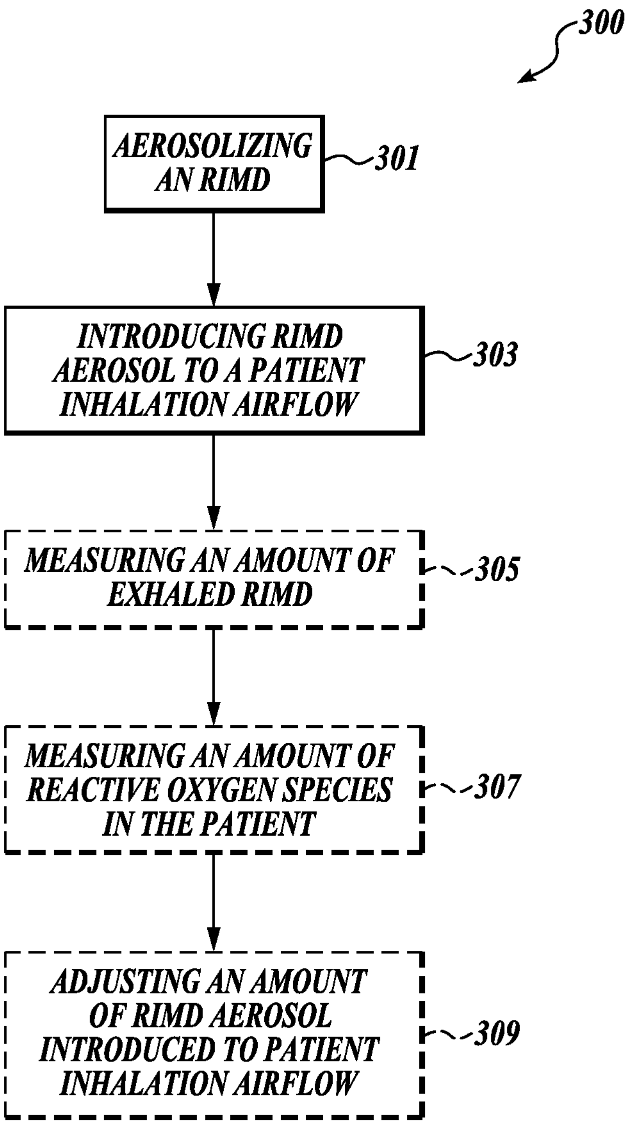
FIG. 3 is a schematic block diagram of a method, in accordance with an embodiment of the disclosure.

In an aspect, the present disclosure provides a method of delivering an aerosol comprising an RIMD to a patient. In that regard, attention is directed to FIG. 3 which is a schematic illustration of a method 300 of delivering an RIMD aerosol to a patient, in accordance with an embodiment of the disclosure. One of ordinary skill in the art having the benefit of the present disclosure will appreciate that the blocks of method 300 may occur in any order and even in parallel. Additionally, blocks may be added to, or removed from, method 300 in accordance with the teachings of the present disclosure.

The method 300 may begin with block 301, which includes aerosolizing an RIMD. As discussed further herein with respect to the devices and system s of the present disclosure, aerosolizing an RIMD provides an RIMD aerosol including RIMD droplets, such as RIMD liquid droplets.

In an embodiment, the RIMD is a fluorinated anesthetic. In an embodiment, the RIMD is selected from the group consisting of isoflurane, sevoflurane, desflurane, methoxyflurane, and combinations thereof. In an embodiment, the RIMD is mixed with an additive selected from the group consisting of pharmacologically acceptable carriers, vehicles, solvents, diluents, coloring agents, preservatives, neutralizers and stabilizers, and combinations thereof. In an embodiment, the RIMD is a liquid at room temperature and atmospheric pressure and not readily miscible with water.

In an embodiment, aerosolizing the RIMD includes operating a device of the present disclosure, such as device 100. In an embodiment, aerosolizing the RIMD includes operating a system of the present disclosure, such as system 200.

Figure 4A:
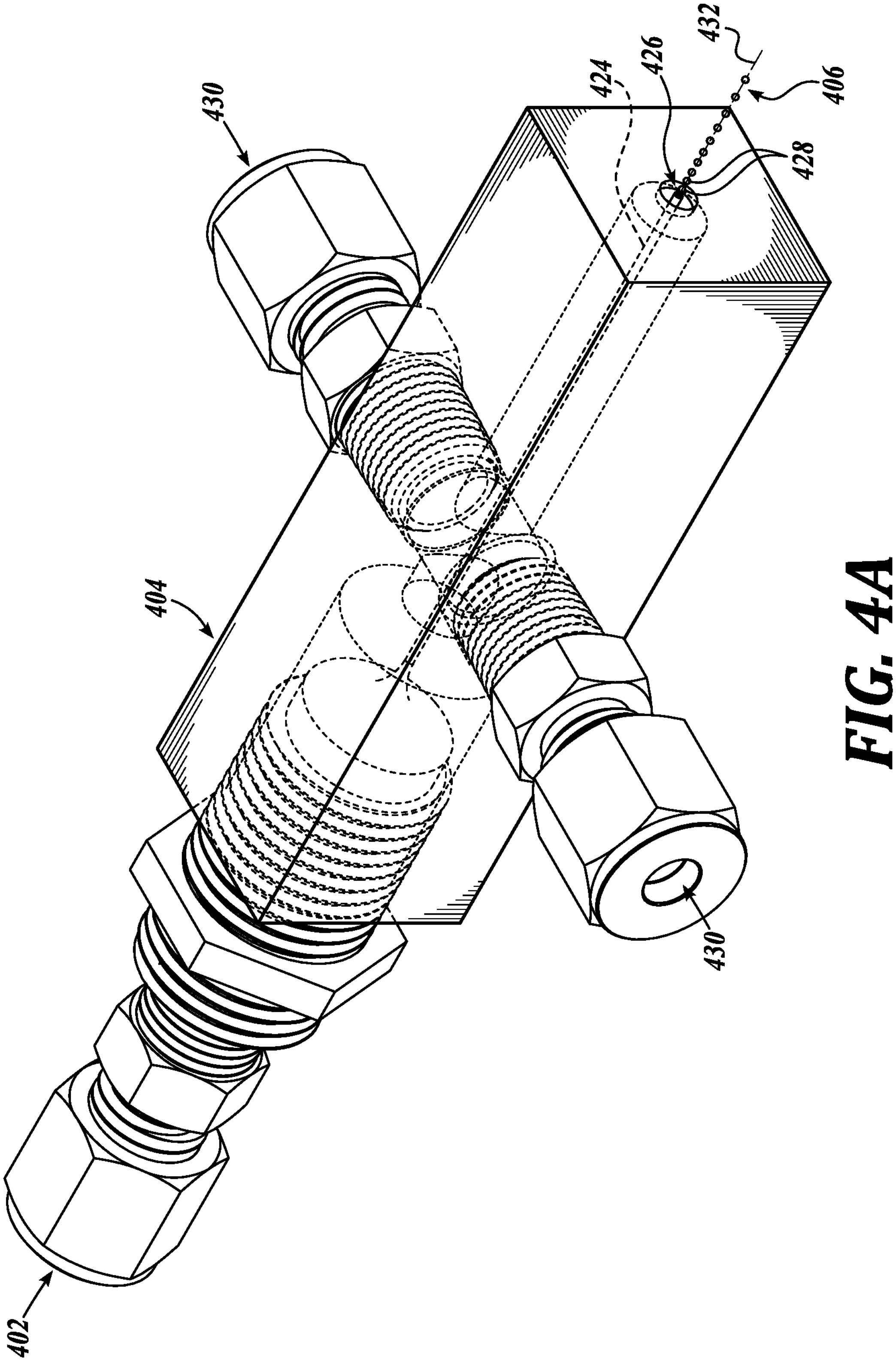
FIG. 4A is a perspective view of an aerosolizer, in accordance with an embodiment of the disclosure.
Figure 4B:
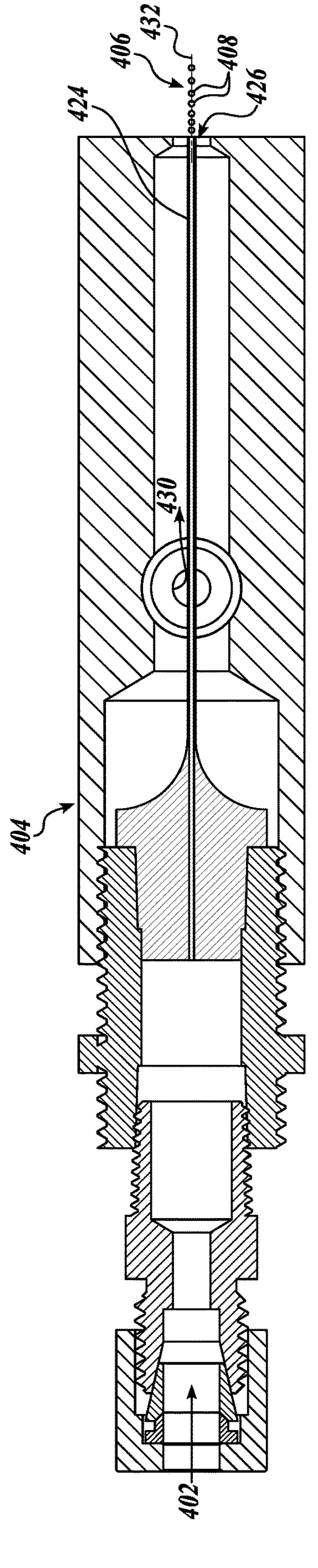
FIG. 4B is a cross-section view of the aerosolizer of FIG. 4A.

In an embodiment, aerosolizing the RIMD includes operating the aerosolizer of FIG. 4. In an embodiment, aerosolizing the RIMD includes dispensing the RIMD through a lumen of a needle; and coaxially moving sheath gas about the needle to generate a plurality of RIMD droplets. As discussed further herein with respect to the devices of the present disclosure and with respect to FIG. 4, such sheath gas exposes the dispensed liquid RIMD to shear forces sufficient to break a stream of liquid RIMD and to generate the liquid RIMD droplets.

In an embodiment, coaxially moving the sheath gas about the needle includes moving the sheath gas at a gas speed in a range of about 20 m/s to about 100 m/s. In an embodiment, coaxially moving the sheath gas about the needle includes moving the sheath gas at a gas speed of about 40 m/s. As discussed further herein, such gas speed may be suitable to generate an RIMD aerosol including RIMD liquid droplets having an average diameter less than 25 μm, such as in a range of about 10 μm to about 20 μm.

Block 301 may be followed by block 303, which includes introducing the RIMD aerosol to a patient inhalation airflow. In an embodiment, introducing the RIMD aerosol into the inhalation airflow of the patient includes transporting the RIMD aerosol with a ventilator. In an embodiment, the ventilator generates airflow to transport the RIMD aerosol. As discussed further herein with respect to FIG. 2, in an embodiment, the ventilator is a portable ventilator, such as one powered by compressed gas and/or a battery.

The terms "patient", "individual" and "subject" include any of vertebrates, mammals, and humans depending on intended suitable use. In some embodiments, the individual is a mammal. In some embodiments, the individual is any one or more of human, bovine, equine, feline, canine, rodent, or primate. In some embodiments, the individual is a human.

As discussed further herein, introducing an RIMD aerosol to a patient inhalation airflow may be suitable to treat reperfusion injury, such as to ameliorate, palliate, lessen, and/or delay one or more of its symptoms, such as those symptoms described herein above. Accordingly, in an embodiment, the patient is experiencing or is at risk for experiencing reperfusion injury. Those experiencing or at risk for experiencing reperfusion injury include, for example, those experiencing or suspected of experiencing conditions selected from the group consisting of cardiac arrest, myocardial infarction, intracranial hemorrhage, traumatic brain injury, stroke, intracranial hemorrhage, hemorrhagic shock, traumatic injury, ARDS, inflammatory bowel disease, vasculitis, inflammatory arthritis, degenerative musculoskeletal or neurologic conditions, sepsis, stroke, traumatic brain injury, spinal cord injury, trauma-induced hypovolemic shock, rheumatoid arthritis, other shock states, and combinations thereof.

In an embodiment, the RIMD aerosol is introduced to the patient inhalation airway shortly after recognition or diagnosis of an ischemic condition, such as recognition of one or more of the conditions described hereinabove. In that regard, in an embodiment, the RIMD aerosol is provided to the patient within 48 hours, with 36 hours, within 24 hours, within 12 hours, within 6 hours, within 5 hours, within 4 hours, within 3 hours, within 2 hours, within 1 hour, within minutes after the recognition of an ischemic condition in the patient and/or ROSC.

In an embodiment, an amount of RIMD aerosol introduced in the patient inhalation airway is based on a duration time of low blood flow or no blood flow of the patient. Such a duration time can be estimated as a duration from onset of cardiac arrest to restoration of blood flow. Generally, the longer the duration the more RIMD aerosol is introduced in the patient inhalation airway.

Block 303 may be followed by block 305, which includes measuring an amount of exhaled RIMD. Such measuring can be performed, for example, with a gas monitor in fluidic communication with an exhalation airflow of the patient. As discussed further herein with respect to the system of FIG. 2, such a measurement of RIMD exhaled by the patient can be an indication of an amount of RIMD in the patient. In an embodiment, block 305 is optional.

In an embodiment, measuring an amount of exhaled RIMD is performed periodically within 72 hours of diagnosis of an ischemic state, reperfusion, and/or of ROSC. In an embodiment, measuring an amount of exhaled RIMD is performed about 30 minutes after diagnosis of an ischemic state, reperfusion, and/or of ROSC. In an embodiment, measuring an amount of exhaled RIMD is performed about 90 minutes after diagnosis of an ischemic state, reperfusion, and/or of ROSC.

Block 305 may be followed by block 307, which includes measuring an amount of reactive oxygen species in the patient. As discussed further herein, one aspect of reperfusion injury can include generation of reactive oxygen species within a patient experiencing reperfusion injury. Such a measurement of reactive oxygen species levels can provide information regarding an extent of reperfusion and/or an effectiveness of reperfusion injury treatment. In an embodiment, block 307 is optional.

In an embodiment, measuring an amount of reactive oxygen species in the patient is performed periodically within 72 hours of diagnosis of an ischemic state, reperfusion, and/or of ROSC. In an embodiment, measuring an amount of reactive oxygen species in the patient is performed about 30 minutes after diagnosis of an ischemic state, reperfusion, and/or of ROSC. In an embodiment, measuring an amount of reactive oxygen species in the patient is performed about 90 minutes after diagnosis of an ischemic state, reperfusion, and/or of ROSC.

Block 305 and/or block 307 may be followed by block 309, which includes adjusting an amount of RIMD aerosol introduced into the patient inhalation airflow. As discussed further herein with respect to the system of FIG. 2, adjusting an amount of aerosol generated can include adjusting a flow rate of a pump in fluidic communication with the RIMD and with an aerosolizer. In an embodiment, adjusting an amount of aerosol generated includes increasing a flow rate of liquid RIMD through the lumen of a needle of an aerosolizer, as discussed further herein with respect to FIG. 4.

In an embodiment, adjusting an amount of the RIMD aerosol introduced in the inhalation airflow is based upon an amount of RIMD in a patient, such as based on a measured amount of RIMD exhaled by the patient. As above, an amount of RIMD in a patient's exhalation airflow may be indicative of an amount of RIMD in the patient. If too much or too little RIMD is present in the patient, an amount of RIMD aerosol introduced may be adjusted, such as to reach an amount of RIMD in the patient suitable for reperfusion injury treatment and/or to avoid toxic levels of RIMD in the patient.

In an embodiment, adjusting the amount of RIMD aerosol introduced in the inhalation airflow is based upon an amount of ROS in a patient, such as a measured amount of ROS in the patient. As above, ROS in a patient may be indicative of an extent of reperfusion injury and/or an effectiveness of reperfusion injury treatment. In this regard, an amount of RIMD aerosol introduced into a patient inhalation airflow may be adjusted if, for example, measured ROS levels are above a predetermined level. Likewise, an amount of RIMD aerosol introduced into a patient inhalation airflow may be reduced or ceased altogether if measured ROS levels are below a predetermined threshold.

Certain processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While illustrative embodiments have been illustrated and described, it will be appreciated that various changes can be made therein without departing from the spirit and scope of the claimed subject matter.

The invention claimed is:

1. A device for delivering an aerosolized reperfusion-injury-modifying drug (RIMD) to a patient, the device comprising:

an RIMD container adapted to contain an RIMD;

an aerosolizer in fluid communication with the RIMD container, the aerosolizer configured to aerosolize the RIMD to provide an RIMD aerosol, wherein the aerosol comprises RIMD liquid droplets; an exit port configured to direct the RIMD aerosol for transport into the patient's airways.

2. The device of claim 1, wherein the exit port is configured to couple with a ventilator.

3. The device of claim 1, wherein the exit port is configured to couple with a supraglottic airway or an endotracheal tube.

4. The device of claim 1, wherein the RIMD is a fluorinated anesthetic.

5. The device of claim 4, wherein the RIMD is selected from the group consisting of isoflurane, sevoflurane, desflurane, methoxyflurane, and combinations thereof.

6. The device of claim 1, wherein the RIMD is a liquid at room temperature and atmospheric pressure and immiscible with water.

7. The device of claim 1, wherein the RIMD is mixed with an additive selected from the group consisting of pharmacologically acceptable carriers, vehicles, solvents, diluents, coloring agents, preservatives, neutralizers, surfactants, stabilizers, and combinations thereof.

8. A system for delivering an aerosolized RIMD to a patient, the system comprising:

an RIMD container adapted to contain an RIMD;

an aerosolizer in fluid communication with the RIMD container, the aerosolizer configured to aerosolize the RIMD to provide an RIMD aerosol, wherein the RIMD aerosol comprises RIMD liquid droplets; and a ventilator configured to generate airflow and coupled to an exit port configured to transport the RIMD aerosol to an inhalation airway of the patient; and an exhalation airflow pathway.

9. The system of claim 8, wherein the exit port is configured to couple with a supraglottic airway or an endotracheal tube.

10. The system of claim 8, wherein the exhalation airflow pathway is configured to direct patient exhalation away from the aerosolizer, the exhalation airflow pathway further comprising a gas monitor configured to contact breath exhaled by the patient and to generate a signal based on an amount of RIMD in the exhaled breath.

11. The system of claim 8, further comprising a controller operatively coupled to the gas monitor, the controller including logic that, when executed by the controller, causes the system to perform operations including:

changing an amount of the RIMD delivered to the aerosolizer, thereby changing an amount of RIMD aerosol generated by the aerosolizer, based on the signal generated by the gas monitor.

12. The system of claim 11, further comprising a pump configured to deliver the RIMD to the aerosolizer.

13. The system of claim 12, wherein changing the amount of RIMD aerosol generated by the aerosolizer includes changing a rate at which the pump delivers the RIMD to the aerosolizer.

14. The system of claim 8, the exhalation airway further comprising a filter configured to sequester RIMD in breath exhaled by the patient.

15. The system of claim 8, wherein the RIMD is a fluorinated anesthetic.

16. The system of claim 15, wherein the RIMD is selected from the group consisting of isoflurane, sevoflurane, desflurane, methoxyflurane, and combinations thereof.

17. A method of delivering an aerosol comprising an RIMD to a patient, the method comprising:

aerosolizing an RIMD to provide an RIMD aerosol comprising RIMD liquid droplets; and introducing the RIMD aerosol into an inhalation airflow of the patient after blood flow in the patient is reestablished, wherein the patient is experiencing or at risk for experiencing reperfusion injury.

18. The method of claim 17, wherein aerosolizing the RIMD comprises:

dispensing the RIMD through a lumen of a needle; and moving sheath gas about an exterior of the needle to generate a plurality of RIMD droplets.

19. The method of claim 17, wherein the patient is experiencing or is at risk for experiencing reperfusion injury.

20. The method of claim 17, wherein the RIMD is a fluorinated anesthetic.

21. The method of claim 20, wherein the RIMD is selected from the group consisting of isoflurane, sevoflurane, desflurane, methoxyflurane, and combinations thereof.

22. The method of claim 17, wherein introducing the RIMD aerosol into the inhalation airflow of the patient includes transporting the RIMD aerosol with a ventilator.

23. The method of claim 17, further comprising:

measuring an amount of RIMD in breath exhaled by the patient; and adjusting an amount of the RIMD aerosol introduced in the inhalation airflow based upon the measured amount of RIMD.

24. The method of claim 17, further comprising:

measuring an amount of reactive oxygen species (ROS) in the patient; and adjusting the amount of RIMD aerosol introduced in the inhalation airflow based upon the measured amount of ROS.

25. The device of claim 1, wherein the aerosolizer is configured to provide the RIMD aerosol including droplets of the RIMD having an average diameter in a range of about 10 μm to about 20 μm.

26. The device of claim 1, wherein the aerosolizer is configured to aerosolize the RIMD to provide a consistent dosage value over time of an RIMD aerosol.

27. The device of claim 26, further comprising a pump configured to deliver the RIMD to the aerosolizer in a controlled manner to provide a consistent dosage value over time of the RIMD aerosol.

* * * * *